United States Patent [19]
Saundry et al.

[11] Patent Number: 4,578,218
[45] Date of Patent: Mar. 25, 1986

[54] PURIFICATION OF FACTOR VIII WITH INSOLUBLE MATRIX HAVING FREE SULFATE GROUPS COVALENTLY BOUND THERETO

[75] Inventors: Richard H. Saundry, London; Geoffrey F. Savidge, Kent, both of England

[73] Assignee: The Special Trustees for St. Thomas' Hospital, London, England

[21] Appl. No.: 699,957

[22] Filed: Feb. 8, 1985

[30] Foreign Application Priority Data

Feb. 9, 1984 [GB] United Kingdom ............... 8403473

[51] Int. Cl.$^4$ ............... C07G 7/00; A61K 35/16; A61K 35/14
[52] U.S. Cl. ............... 260/112 B; 424/101
[58] Field of Search ............... 260/112 B; 424/101

[56] References Cited

U.S. PATENT DOCUMENTS

| | | | |
|---|---|---|---|
| 3,920,625 | 11/1975 | Andersson et al. | 260/112 B |
| 4,022,758 | 5/1977 | Andersson et al. | 260/112 B |
| 4,210,580 | 7/1980 | Amrani | 260/112 B |
| 4,278,594 | 7/1981 | Amrani | 260/112 B |
| 4,361,509 | 11/1982 | Zimmerman et al. | 260/112 B |
| 4,395,396 | 7/1983 | Eibl et al. | 424/101 |
| 4,397,841 | 8/1983 | Johnson | 424/101 |
| 4,471,112 | 9/1984 | Johnson | 424/101 X |
| 4,522,751 | 6/1985 | Linnau et al. | 260/112 B |

FOREIGN PATENT DOCUMENTS

| | | | |
|---|---|---|---|
| 883549 | 11/1961 | United Kingdom | 424/85 |
| 2080312 | 2/1982 | United Kingdom . | |

OTHER PUBLICATIONS

Introduction to Modern Biochemistry, 3rd Ed. Karlson (1970), pp. 326–327.

Primary Examiner—Howard E. Schain
Attorney, Agent, or Firm—Cushman, Darby & Cushman

[57] ABSTRACT

Factor VIII is purified by adsorption onto a insoluble matrix having free sulphate groups, such as dextran sulphate, and selective elution therefrom.

A suitable eluant for the purification of the von Willebrand protein (Factor VIIIR:vWp) is citrate buffer, pH 6.85, containing 0.47 M sodium chloride and 2.14 mM calcium chloride.

A suitable eluant for the purification of the Factor VIII complex (Factor VIIIR:Ag, Factor VIIIR:vWp and Factor VIII:C) is citrate buffer at pH value between 6.2 and 7.3 containing 1.0 M glycine, 2.14 mM calcium chloride and 0.5 M sodium chloride at +4° C.

11 Claims, No Drawings

PURIFICATION OF FACTOR VIII WITH INSOLUBLE MATRIX HAVING FREE SULFATE GROUPS COVALENTLY BOUND THERETO

This invention relates to the purification of the Factor VIII complex comprising the Factor VIII clotting factor and/or the Factor VIII-related von Willebrand protein.

Factor VIII is a blood protein complex which participates in the early stages of blood coagulation. It circulates in trace amounts in normal plasma as a high molecular weight glycoprotein. This complex is made up of a procoagulant component (Factor VIII:C) which is biologically inactive or absent in haemophilia A, and a further component called Factor VIII-related von Willebrand protein (Factor VIIIR:vWp), which is associated with platelet aggregation and adhesive properties. This latter protein is quantitatively or qualitatively altered in the plasma of patients suffering from von Willebrand's disease. The complex in vivo is believed to be associated with lipoproteins which probably confer additional stability. Furthermore, optimum concentrations of calcium ions are believed to confer additional stability to the Factor VIII:C moiety.

The haemorrhagic symptoms of haemophilia A or of von Willebrand's disease are treated by the administration of Factor VIII from healthy donors. This can be done through transfusion of whole plasma in mild cases, or by intravenous administration of "cryoprecipitate" in more severe cases. Cryoprecipitate is usually obtained by the procedure of Pool et al (Nature 203:312 (1964)). This involves freezing the plasma and then allowing it to thaw slowly at 4° C., which results in the formation of cryoprecipitate that can be readily re-dissolved at 37° C. The vast majority of the Factor VIII in plasma is recovered in the cryoprecipitate, which thus provides a convenient source of concentrated Factor VIII for therapeutic purposes.

The treatment of Haemophilia A and von Willebrand's disease with whole plasma or cryoprecipitate carries some serious drawbacks. For example, it is difficult to ensure that whole plasma is free from infectious organisms, such as the viruses responsible for hepatitis and those believed to be responsible for the acquired immune deficiency syndrome (AIDS). Any such organisms are also likely to be carried through into cryoprecipitate obtained from infected plasma.

Considerable research effort has been expended therefore on the purification of the Factor VIII complex. Whilst this has resulted in the purification of both Factor VIII:C and of Factor VIIIR:vWp, the reported purification procedures have involved many separate purification steps, resulting in low yields (see Baugh et al, Biochimica Biophysica Acta 371:360 (1974); and Olson et al., J. Lab. Clin. Med. 89:1278 (1977), reporting yields of only 20–40%).

The present invention provides an economically attractive process for purifying both Factor VIII:C and Factor VIIIR:vWp. According to the present invention there is provided a process for the purification of the Factor VIII complex, comprising adsorbing an impure preparation of Factor VIII onto an affinity matrix having free sulphate groups, and subsequently selectively eluting the desired factor components.

GB-A-2080312 discloses the use of an insoluble sulphated matrix (dextran sulphate agarose) for the chromatographic separation of coagulation Factors II, VII, IX and X and a Factor VIII-inhibitor-bypassing activity (believed to be Factor IXa). These are the so-called vitamin K-dependent clotting factors, which are structurally related to each other. Factor VIII, however, is structurally quite distinct from these Factors, and it was most unexpected that it too would bind to an insoluble sulphated matrix such as dextran sulphate agarose. That the binding of the Factor VIII complex to dextran sulphate agarose is indeed surprising is further illustrated by EP-A-0022052. This specification discloses a procedure for the purification of blood clotting factors, which procedure relies on the alleged failure of Factor VIII:C to bind to sulphated mucopolysaccharides under the conditions specified.

The advantages of the process of the present invention as compared with existing methodology for the purification of Factor VIII include the high yields produced (for example, from 30–50% of the biologically active Factor VIII:C, and from 70–80% of the Factor VIIIR:vWp in the starting material), the separation of biologically active from inactive material, the preservation of the higher molecular weight multimer forms which are believed to be implicated in the Factor VIIIR:vWp activities, an increased commercial potential in the form of its simplicity, its applicability for batch procedures, and the absence of any requirement for sophisticated laboratory equipment. The purified product contains low levels of both fibrinogen and of fibronectin. These two proteins are believed to prevent easy reconstitution of existing Factor VIII preparations.

Suitable sulphate-containing matrices include dextran sulphate, or chondroitin sulphate and sulphated agarose, optionally coupled to a support matrix such as agarose or glass beads. The preferred medium is dextran sulphate, which can be of widely varying molecular weight, such as 3,500 to 500,000 daltons. The use of a support matrix such as agarose gives a medium of more robust structure.

Adsorption of the mixture, and subsequent selective elution of Factor VIII, can be conducted either batchwise or in a conventional chromatographic column. Selective elution of adsorbed proteins can be achieved by washing the sulphate-containing matrix with aqueous solutions of increasing salt concentration, at either constant or different pH values: the salt concentration can be varied continuously (for example, linearly) or discontinuously.

Preferably, the Factor VIII is eluted using salt solutions of increasing ionic strength at a constant pH of from 6.0 to 8.0, and most preferably at a pH of from 6.2 to 7.4. The buffer is preferably citrate, and calcium chloride is preferably also included. It has been found that low concentrations (e.g. 2 to 5 mM) of calcium chloride assist in recovering high yields of Factor VIII:C.

A particularly preferred eluant for the purification of Factor VIII R:vWp is citrate buffer, pH 6.85, containing about 0.47 M sodium chloride and about 2.14 mM calcium chloride. A preferred eluant for the purification of the Factor VIII complex (factor VIII R:Ag; Factor VIIIR:vWp and Factor VIII:C) is citrate buffer at a pH between 6.2 and 7.3, containing about 1.0 M glycine, about 2.14 mM calcium chloride, and about 0.5 M sodium chloride.

High yields of Factor VIII:C are achieved if the whole procedure is performed at reduced temperature, for example 4° C. However, we have found that binding of Factor VIII complex to sulphated matrices is slow at 4° C., and it is therefore preferred that the initial adsorption be carried out at a temperature of 10° to 30° C., for example 20° C.

The source of crude Factor VIII can be whole human plasma, which may be used directly in the process of the present invention. The highest yields are obtained with whole plasma. If desired, however, the plasma may be partially purified and/or concentrated (e.g. by cryoprecipitation) before being purified (or further purified) by the process of this invention.

Although the overall yields of Factor VIII obtained from cryoprecipitate are often lower than when plasma is used, it is the preferred starting material since the cryosupernatant can conveniently be employed for the purification of other commercially important blood proteins such as the Vitamin-K dependent clotting factors and albumin.

Purification of Factor VIII in accordance with the present invention is further described in the Examples below. The methods used in these Examples for measuring Factor VIII and other activities are as follows:

Factor VIII:C, the Pro-coagulant Factor

The Factor VIII:C activity in unknown samples is estimated by measuring its ability to correct the clotting time of Factor VIII:C deficient plasma. A two-stage commercial Factor VIII assay kit (Diagnostic Reagents Ltd., Thame, Oxon, England) is used in these investigations. This is based on the procedure developed by Denson K. W. E. (Trans. of the International Committee on Haemostasis and Thrombosis, Chapel Hill, North Carolina, U.S.A. December 1966) based on the two-stage thromboplastin generation test of Biggs, Eveling and Richards, 1955. Briefly, serial dilutions of the test materials and of standard normal pooled plasma as control are incubated at 37° C. for ten minutes with normal serum, phospholipid and clotting Factor V. The mixtures are then subaliquoted into normal substrate plasma and the time taken for the fibrin clot to form is measured. A direct linear relationship is found between the clotting time and the concentration of Factor VIII:C.

The Ristocetin Co-factor Assay

In addition to the procoagulant activity of Factor VIII (Factor VIII:C), the Factor VIIIR:vWp in the Factor VIII complex expresses platelet aggregating activity in the presence of the obsolescent antibiotic, ristocetin. This activity is referred to as the Ristocetin Co-Factor Activity (Factor VIIIR:CoF), and is widely believed to be the equivalent of the von Willebrand Factor Activity, Factor VIIIR:vWp. In the assay, normal platelets, fixed chemically with formalin, are mixed with the test samples and the antibiotic ristocetin is added, inducing aggregation of the platelets. The time course of this aggregation can be followed by light transmission principles with a good correlation between the initial velocity of aggregation and the amount of Factor VIII:vWp in the test samples. By comparison with test samples of known standard Factor VIIIR:vWp concentration, the amount of Factor VIIIR:vWp in the unknown samples can be calculated.

Immunoassay Methods (1) Electroimmuno-Assay

Highly purified human Factor VIII complex can be used to raise heterologous antisera in rabbits with high titre activity directed against the Factor VIII molecules. Such antisera invariably react with human Factor VIII to produce precipitates if the correct ratio of Factor VIII to antiserum concentration is achieved. This phenomenon can be utilised to develop moderately sensitive techniques for the estimation of antigenic determinants (Factor VIIIR:Ag) on the Factor VIIIR:vWp. In the conventional immunoelectrophoretic method (Laurell, C.B., (1966) Analytical Biochemistry 15:45) the specific antiserum is incorporated into agarose gels through which the Factor VIII can be electrophoresed. As the proteins migrate they interact with the antiserum causing precipitates to form. After a suitable time the electrophoresis is stopped and the protein precipitates fixed and stained. The antibody-antigen complexes are visualised as "precipitation rockets" where their heights are proportional to the amount of Factor VIII antigen present in the original samples.

A modification of this technique can be used from which it is possible to glean qualitative information about the sizes of the Factor VIII complexes in any given sample. This technique is known as "two-dimensional crossed electrophoresis" (2 DCIE). The sample is electrophoresed through agarose gel in the absence of added antiserum when the migration observed is proportional to the size of the molecules. After a suitable period, the proteins are re-electrophoresed (in a direction perpendicular to the first electrophoresis) into a second agarose gel into which the antiserum has been incorporated. After fixing and staining the lines of precipitation, the distance moved by the Factor VIII in the first dimension can be measured, and the molecular size estimated.

(2) Enzyme-linked immuno assay (ELISA)

Heterologous rabbit antiserum with high titre activity directed against human Factor VIIIR:Ag is immobilised in the wells of specially designed microtitre plates at alkaline pH. After removal of excess antiserum, serial dilutions of test and standard samples are incubated with these plates at neutral pH in the presence of detergent to prevent non-specific adsorption to the surface. The plates are thoroughly washed free of unbound sample and then allowed to react with more of the same antiserum, but where the antibodies have been previously chemically coupled to the enzyme, horseradish peroxidase.

The amount of enzyme-linked antiserum bound to the plates is directly related to the amount of Factor VIIIR:Ag in the wells and which had been immobilised by the first antiserum. This can be quantitated through use of a chosen specific enzyme substrate and measuring the amount of coloured product by light absorption principles. The virtues of the ELISA technique are that it is less time consuming, more economic in the use of the heterologous antiserum, and equally sensitive compared with the conventional electroimmunoassay method.

(3) The Radioimmuno Assay (RIA)

Highly purified Factor VIIIR:vWp was prepared by the process of the present invention, and radiolabelled with $^{125}I$ by a modification of the iodine monochloride method. This labelled material could then be used in a competitive assay for Factor VIII:vWp when a limiting amount of rabbit antiserum specific for human Factor VIIIR:vWp was allowed to compete in mixtures of labelled and unlabelled material. The antibody-antigen complexes were separated from the unbound antigen (excess Factor VIIIR:vWp) and counted for radioactivity. There is an inverse correlation between the radioactivity recovered in the complexes and the amount of Factor VIIIR:vWp present in the test samples. Factor VIIIR:vWp levels could then be calculated using standard curves constructed from the results obtained with serial dilutions of standard Factor VIIIR:vWp concentrates. The great advantage of the RIA compared with conventional immunoelectrophoretic methods is a much greater sensitivity, allowing accurate estimation of Factor VIIIR:vWp levels of the order of 0.1% of that found in normal plasma samples.

(4) The Multimer Sizing Technique

Factor VIIIR:vWp is known to circulate in normal plasma as polymeric (multimeric) aggregates of the basic Factor VIII molecular complex. Factor VIII/von Willebrand factor/ristocetin co-factor activity is belived to be associated only with the larger multimeric forms, which are absent or reduced in the plasma from von Willebrand disease patients. These multimeric forms can be identified by using a modification of the multimer sizing technique of Ruggeri and Zimmerman (Z. M. Ruggeri and T. S. Zimmerman (1981) Blood 57:1140–1143; M. S. Enayat and F. G. H. Hill (1983) J. Clin. Pathol. 36:915–919).

Briefly, the various multimeric Factor VIII forms are pre-treated with 8 M urea/2% sodium dodecyl sulphate in order to dissociate the various multimeric forms from each other, and these are separated according to their relative sizes by electrophoresis into 0.8% agarose/2.5% polyacrylamide gel. The proteins are then fixed and exhaustively washed, followed by incubation with radio-labelled antiserum specific for Factor VIII. Excess unbound antiserum is removed by washing, and the Factor VIII/radio-labelled anti-Factor VIII complexes are visualised in the gels by autoradiographic tehchniques, whereupon intensity of exposure of the X-ray film, and relative mobility of the Factor VIII:vWp molecules during the electrophoretic procedures provide information on the number, concentration and size of the multimeric forms of Factor VIII present in the original sample. An alternative method has been developed to locate and quantitate the protein separated by the electrophoretic procedures. After fixing and exhaustively washing with distilled water, the gel is first incubated with rabbit anti-human Factor VIIIR:Ag in phosphate buffer containing 0.1% of the detergent Tween 20, and after removing excess unbound rabbit antiserum, the gel is incubated with swine anti-rabbit immunoglobulin followed by incubation with peroxidase-linked rabbit immunoglobulin. After exhaustive washing, the gel is overlaid with 0.05% of the enzyme substrate diaminobenzidine and 0.2% hydrogen peroxide. When staining is complete the gel can be washed, dried and stored, and the bands visualised by conventional photography or quantitated by measuring the colour intensity of the stained bands by standard scanning spectrophotometric techniques.

(5) The Immunoradiometric Assay for Factor VIIIC:Ag

Poly-transfused severe haemophiliac patients sometimes develop inhibitors against normal Factor VIII:C. Such inhibitors were demonstrated to be immunoglobulin (IgG) antibodies, can be isolated from the plasma of such patients and used in a sensitive method for the quantitation of the antigen (Factor VIIIC:Ag) associated with the Factor VIII:C activity. The purified IgG molecules with anti-Factor VIIIC:Ag activity are digested with the proteolytic enzyme pepsin under reducing conditions yielding low molecular active fragments (Fab/) which still retain their anti-Factor VIIIC:Ag activities. Such preparation can be radiolabelled with $^{125}$I by conventional methods and added in excess to suitable dilution of test samples. After incubation at 37° C. for 4 hours the proteins including the high molecular weight Factor VIIIC:Ag-Fab/ complexes are selectively precipitated with 38% saturated ammonium sulphate. The radioactivity in these precipitates is measured. There is good correlation between the amount of Factor VIIIC:Ag in the sample and the amount of radioactivity recovered in the precipitates. Absolute levels can be estimated through comparison with dilutions of standard Factor VIIIC:Ag-containing samples carried through the whole assay procedure at the same time.

The Platelet Binding Assay

Radio-labelled Factor VIIIR:vWp can be utilised in an extremely sensitive assay for binding Factor VIII to formalin-fixed platelets in the absence of ristocetin. Platelets are isolated from the plasmas of normal donors, fixed with formalin, and stored at −80° C. until required. Known amounts of $^{125}$I-labelled Factor VIII are added to test samples and allowed to compete with the "cold" Factor VIII for a limiting number of platelets in the presence of ristocetin at 37° C. After half an hour the platelets are removed by centrifugation and suitable aliquots of the supernatant taken for radioactive measurements.

The recovery of isotope in the supernatants is proportional to the amount of Factor VIIIR:vWp in the test samples, and absolute amounts can be computed by reference to a standard curve constructed from data obtained using standard Factor VIIIR:vWp samples.

Measurement of Proteolytic Enzyme Activities

The Factor VIII complex is susceptible to inactivation by contaminating proteolytic enzyme activity. Many of these enzymes may become activated during the procedures adopted in this invention and contamination of the final product may limit its usefulness in therapeutic procedures. The more likely contaminants in Factor VIII preparations are believed to be thrombin (Factor IIa) and activated clotting Factor X (Factor Xa), plus the contact factors (Factors XIa and XIIa). Proteolytic enzyme activities can be estimated using specific chromogenic substrates (S2222 designed to measure Factor Xa activity, S2238 for thrombin, and S2302 for plasma kallikrein). The substrates were obtained commercially from KabiVitrum AB, Stockholm, Sweden and used by a modification of the manufacturer's recommended procedure in microtitre plates, monitoring the enzyme kinetics by spectrophotometric absorption principles.

High Performance Liquid Chromatography (HPLC)

Factor VIII-containing fractions resulting from the chromatography procedures using the affinity matrices used in this invention, were investigated for protein molecular weight distribution by high performance liquid chromatography (HPLC) using either TSK-SWG-4000 (void exclusion molecular weight 1,000,000 daltons) or TSK-SWG-3000 (void exclusion molecular weight 500,000) gel filtration columns (Beckman RIIC, High Wycombe, Bucks. England). These columns were variously run at either 0.5 or 1.0 ml per min. and developed with buffers comprised of 14 mM trisodium citrate, 2.14 mM calcium chloride, 0.15 M sodium chloride pH 7.0.

Enzyme linked Immunoassays (ELISA) for other plasma protein

High titre antisera with great specifity directed against various antigens are commercially available. Using the same principles elaborated for the ELISA assay for Factor VIIIR:Ag, specific ELISA tests were developed for the measurement of the antigens assocaited with the normal plasma proteins fibrinogen, fibronectin (cold insoluble globulin, CIG), plasminogen, immunoglobulin G (IgG), immunoglobulin M (IgM), clotting Factor IX, α-lipoproteins (HDL$_2$, molecular weight 350,000 daltons, and HDL$_3$, molecular weight 250,000 daltons) and β-lipoprotein (VLDL, molecular weight greater than 10,000,000 daltons, and LDL, molecular weight 3,000,000 daltons).

EXAMPLE 1

Purification of Factor VIIIR:vWp from cryoprecipitate by column chromatography

An aqueous solution of dextran sulphate (15 mg/ml) was prepared by dissolving dextran sulphate of apparent molecular weight of 500,000 daltons (Pharmacia Fine Chemicals, Uppsala, Sweden). 360 ml. of the dextran sulphate solution was added to 600 ml. of settled washed Sepharose 6B or Sepharose 4B (Pharmacia Fine Chemicals, Uppsala, Sweden) and cooled with stirring to +4° C. in a reaction vessel cooled in ice. The pH was adjusted to 11.0, and 12 gm cyanogen bromide added and stirred. The pH was maintained between 10.0 and 11.3 by the addition of 4N sodium hydroxide and the reaction allowed to proceed for 45 minutes at 4° C. Addition of sodium hydroxide was stopped, and the reactants were allowed to warm to room temperature under constant stirring and the pH value allowed to stabilise at 8.5. The mixture was allowed to stand overnight at ambient room temperature, after which the resin was washed with 0.2 M sodium borate/0.5 M sodium chloride pH 8.5, and then subsequently with 0.2 M sodium acetate/0.5 M sodium chloride pH 4.0. The resin was poured into a siliconised glass column and equilibrated with 14 mM trisodium citrate, 2.14 mM calcium chloride and 0.15 M sodium chloride pH 6.85. The cryoprecipitate obtained from individual donations of citrated whole blood was redissolved in approximately 40 mls. of the equilibrating buffer and treated with 1/10 volume of aluminium hydroxide (0.25 gm/ml) for three minutes at 37° C. to remove the Vitamin K dependent clotting factors. The aluminium hydroxide was removed by centrifugation and the supernatant applied to the column and eluted at room temperature until the optical density at 280 mn of the eluate was the same as in the eluting buffer. A linear salt gradient of 0.15-1.0 M sodium chloride in 14 mM trisodium citrate, 2.14 mM calcium chloride at pH 6.85 was then applied and the Factor VIIIR:vWp sharply eluted as a single component at a salt concentration of approximately 0.47 M sodium chloride. The Factor VIIIR:vWp was observed to elute subsequent to any detectable amounts of fibrinogen, Factor IXa and Factor XI. Trace amounts of fibronectin, Factor VIII:C (up to 1% of the total amount applied to the column) and Factor VIIIR:Cag (up to 5% of the total amount) were present in the ascending limb of the Factor VIIIR:vWp peak. The yield of the Factor VIIIR:vWp represented approximately 85% of the Factor VIIIR:vWp applied to the purification system. The protein was demonstrated to be in high multimeric form and contained approximately 65% of the applied Factor VIIIR:Ag content of the initial material: the other 35% of the Factor VIIIR:Ag being located in the initial void fraction but with undetectable Factor VIIIR:vWp activity along with the Factor VIIIC:Ag which possessed only a fraction (<5%) of the initial VIII:C activity.

EXAMPLE 2

Purification of Factor VIIIR:vWp from whole plasma by column chromatography 100 mls of fresh platelet-poor plasma was absorbed with 10 mls. of aluminium hydroxide solution (0.25 gm/ml) for three minutes at 37° C. and the aluminium hydroxide removed by centrifugation. This absorbed plasma was then mixed with an equal volume of equilibrating buffer consisting of 0.15 M sodium chloride, 14 mM trisodium citrate and 2.14 mM calcium chloride pH 6.85. This was applied to a 65×1.8 cm column of dextran sulphate coupled to Sepharose 4B (prepared as in example 1) and developed with eluting buffers at 36 ml/hr collecting 10 ml. fractions at room temperature. After buffer washing the matrix a linear gradient from 0.15-0.80 M sodium chloride was applied and the fractions corresponding to Factor VIIIR:vWp eluted at 0.47 M sodium chloride. The final yield of Factor VIIIR/vWp was found to be 90% of the activity applied to the column.

EXAMPLE 3

Purification of Factor VIIIR:vWp from whole plasma by salt-gradient chromatography using alternative salts to sodium chloride The procedures adopted in Example 2 were modified to purify Factor VIIIR:vWp from whole platelet-poor plasma but substituting other salts in the gradients in place of sodium chloride. In order to facilitate location of the peaks containing Factor VIIIR/vWp 1.0 ml of radiolabelled Factor VIIIR:vWp was added to 2 ml plasma (subsequent to treatment with aluminium-hydroxide) plus 7 mls. initial buffer and applied to a 30×0.9 cm column of the dextran sulphate- Sepharose 4B matrix, and developed at ambient room temperature. Two identical columns were run in parallel to enable direct comparison of the salt under investigation with the effect of sodium chloride. The initial buffer consisted of 14 mM trisodium citrate and 2.14 mM calcium chloride pH 6.85. The salt-containing buffer gradients always comprise the initial buffer plus the chosen salt concentration at pH 6.85. Peaks of radioactivity were checked for Factor VIIIR:Ag by electroimmunoassay, Factor VIII platelet binding activity and Factor VIIIR:CoF activity. In all cases the peak of radioactivities developed by the salt gradients coincided with the measurable Factor VIII activities. The radiolabelled material behaved identically to the Factor VIIIR:vWp in the plasma in the chromatography procedure. The chosen salts caused elution of the Factor VIIIR:vWp at different concentrations: the molarity of salt at which the peak of activity was eluted using different salt gradients is shown in Table 1. In this series of experiments the pH value was maintained at pH 6.85 which was the pH at which the strongest affinity of Factor VIII in sodium chloride had been observed. The only exception was when ammonium bicarbonate was investigated when the gradient was run from 0.05 to 1.2 M ammonium bicarbonate pH 7.7. Many soluble salts can be substitued for sodium chloride in the gradients used to elute Factor VIIIR:vWp from the matrix.

TABLE 1

| SALT | | MOLARITY AT WHICH VIIIR:vWp ELUTED |
|---|---|---|
| SODIUM CHLORIDE | NaCl | 0.464 |
| LITHIUM CHLORIDE | LiCl | 0.944 |
| POTASSIUM CHLORIDE | K Cl | 0.286 |
| AMMONIUM CHLORIDE | $NH_4Cl$ | 0.733 |
| MAGNESIUM CHLORIDE | $Mg Cl_2$ | 0.427 |
| SODIUM FLUORIDE | NaF | 0.733 |
| SODIUM BROMIDE | Na Br | 0.381 |
| SODIUM FORMATE | $Na HCO_2$ | 0.575 |
| AMMONIUM FORMATE | $NH_4 HCO_2$ | 0.730 |
| SODIUM ACETATE | $Na CH_3 CO_2$ | 0.644 |
| SODIUM SULPHATE | $Na_2 SO_4$ | 0.354 |
| AMMONIUM SULPHATE | $(NH_4)_2 SO_4$ | 0.420 |
| AMMONIUM BICARBONATE | $NH_4 HCO_3$ | 0.529 |

EXAMPLE 4

Purification of the Factor VIII complex from plasma by ammonium chloride gradient column chromatography The dextran sulphate Sepharose 4B matrix prepared as in Example 1 was poured into two identical 30×0.9 cm siliconised class columns and equilibrated with 14 mM trisodium citate/2.14 mM calcium chloride at 4° C. at a constant flow rate of 20 ml per hour. 9 vols. fresh citrated platelet-poor plasma was treated with 1 volume of aluminium hydroxide (0.25 mg/ml) at 37° C. for 3 minutes and the aluminium hydroxide removed by centrifugation. 10 ml. of the aluminium hydroxide-absorbed plasma and 10 ml. of unabsorbed plasma were each separately added to the two columns and eluted in parallel using the same gradient for both columns. After the void material had been eluted a linear salt gradient comprising 380 ml. equilibrating buffer and 380 ml the same buffer containing 0.8 M ammonium chloride was run through both columns simultaneously. The 3.5 ml. fractions were screened for Factor VIIIR:Ag, Fibrinogen, Fibronectin, Factor VIIIR:CoF, Factor VIIIC:Ag and Factor VIII:C content and total yields calculated compared to plasma samples that had been incubated throughout the duration of the experiments at 4° C. None of the proteins investigated was found in the void material eluting from the columns and both columns gave identical profiles. Fibrinogen eluted as a sharp peak at 0.20 M ammonium chloride, fibronectin at 0.33 M ammonium chloride and Factor VIIIR:CoF/Factor VIIIR:Ag at 0.53 M ammonium chloride. The Factor VIIIC:Ag was partially dissociated from the bulk of the Factor VIIIR:Ag and eluted firstly as a small peak of activity along with the fibrinogen and secondly as a second major peak eluting just before, but overlapping with the Factor VIIIR:Ag/R:CoF peak at 0.45 M ammonium chloride. This latter Factor VIIIC:Ag peak contained significant amounts of active Factor VIII:C (as assessed by the 2-stage assay). Overall yields were 86% Factor VIIIR:Ag, 50% Factor VIIIC:Ag, 100% Factor VIIIR:CoF, 50% fibrinogen and 75% fibronectin. The overall yield of Factor VIII:C was 25% when the aluminium hydroxide absorbed material was used, but only 10% when unabsorbed material was used.

The greater part of the kallikrein and thrombin-like enzyme activities were found not to be adsorbed to the column and were eluted with the void fraction. The fractions corresponding to the Factor VIIIR:vWp and the Factor VIII:C contained only traces of kallikrein and thrombin-like enzyme activity. These levels had been reduced through treatment with aluminium hydroxide. There were still significant amounts of Factor Xa-like activity, but following precipitation of the proteins in the fraction using 10% (w/v) polyethyleneglycol 6000 at 4° C., this Factor Xa activity remained in the supernatant with good recovery of the Factor VIII in the precipitates.

EXAMPLE 5

Purification of the Factor VIII complex from cryoprecipitate by sodium chloride gradient column chromatography A 60×1.6 cm siliconised glass column was filled with the dextran sulphate linked Sepharose 4B as in Example 1 and equilibrated at 4° C. at 36 ml per hour with 14 mM trisodium citrate, 2.14 mM calcium chloride pH 6.85. 100 ml blood from a normal donor was collected into 1/10 volume of 3.8% trisodium citrate and platelet-poor plasma obtained following centrifugation at 2000×g at 4° C. for 30 minutes. The plasma was made into six separate aliquots of 10 ml in polypropylene tubes and stored overnight at −80° C. Subsequent to thawing at 4° C. and following centrifugation at 4° C. at 2000×g for 30 minutes the supernatant was discarded. To the resulting cryoprecipitate in each tube, resuspended in 5 ml of equilibrating buffer at 37° C., was added 1 ml of a (50% vol/vol) suspension of gelatin that had been coupled to Sepharose 4B following the procedure of Cuatrecasas P, Wilchek M and Anfinsen C. B. (1968) Proc. Nat. Acad. Sci. U.S. 61:6367–643, and previously equilibrated with the same buffer. After mixing, the tubes were further incubated at 37° C. for fifteen minutes prior to centrifugation at 3300×g for 10 minutes at 37° C. 5 ml of the supernatant from each of the six tubes were removed, combined and applied to the chromatography column. After elution of unbound material was judged to be complete a linear sodium chloride gradient comprising 180 ml initial buffer and 180 ml. 0.8 M sodium chloride was used to develop the bound proteins, collecting 4.0 ml fractions. Factor VIII eluted as a single sharp peak at 0.52 M sodium chloride with a total yield 87% Factor VIIIR:Ag, 85% Factor VIIIR:-CoF, 75% Factor VIIIC:Ag and 44% Factor VIII:C. This was completely resolved from all the plasminogen that was shown to elute at 0.15 M NaCl, from the bulk of the fibrinogen that eluted as two distinct components at 0.295 M sodium chloride and 0.375 NaCl, and from the Factor IX which eluted at 0.40 M NaCl. Little fibronectin was found indicating that the initial treatment with gelatin-Sepharose was effective in removing in excess of 98.5% of the fibronectin present in the original cryoprecipitate. Immunoglobulin G (IgG) was detected in many fractions, especially the void material eluting from the column, but less than 1% of the total recovered IgG was found in those fractions containing Factor VIII. Immunoglobulin M was found to elute subsequent to the Factor VIII at 0.62 M sodium chloride. The peak activity of proteolytic enzyme activity measured using the chromogenic substrate S2222 indicated that most of the Factor Xa-like activity eluted coincidentally with the first of the fibrinogen peaks at 0.295 M sodium chloride. The fractions corresponding to Factor VIII contained detectable levels of proteolytic enzyme activity measured with S2222 (Factor Xa) (about 10% of that found in the total eluate from the column) and S2238 (thrombin, about 25% of that found in the total eluate). These proteolytic enzyme activities were not precipitated by treatment at 4° C. with 10% (w/v) polyethylene glygol 6000. This treatment quantitatively precipitated all the Factor VIII. The only other major proteins found to be present in the Factor VIII preparation were various types of lipoproteins. These could be separated from the Factor VIII by ultracentrifugation methods.

EXAMPLE 6

Purification of the Factor VIII complex from cryoprecipitate by column chromatography using a linear sodium chloride gradient combined with concave decreasing pH gradient A 60×1.6 cm siliconised glass column was filled with dextran sulphate linked to Sepharose 4B, prepared as in Example 1, and equilibrated with 14 mM trisodium citrate, 2.1 mM calcium chloride and 0.075 M sodium chloride pH 7.3 at 4° C. Two whole bags of Blood Transfusion Services cryoprecipitate were thawed at 37° C., total volume 40 mls and made up to 100 mls with equilibrating buffer. The solution was then titrated to pH 7.3 using 50 mM hydrochloric acid and centrifuged at room temperature at 2000×g for fifteen minutes to remove any precipitate. 20 ml of the resulting supernatant was diluted to 50 ml with more equilibrating buffer and applied to the column and eluted at 42 ml per hour. When the unbound material was judged to have finished eluting the proteins were developed using a two chamber linear salt gradient comprising 450 ml. 0.15 M sodium chloride, 14 mM trisodium citrate, 2.1 mM calcium chloride pH 7.6 and 450 ml. 1.00 M sodium chloride, 14 mM trisodium citrate, 2.1 mM calcium chloride pH 5.8 at 4° C. This gradient was linear with respect to sodium chloride concentration and concave with respect to pH. Good separation of the Factor VIII complex from the other bound proteins was achieved : fibrinogen eluted as a single component at 0.30 M sodium chloride pH 6.9, fibronectin at 0.42 M sodium chloride pH 6.63 and Factor VIII at 0.51 M sodium chloride pH 6.4. The yield of Factor VIII compared to the total amount applied to the column was 65% Factor VIIIR:Ag 65% Factor VIIIC:Ag with 35% Factor VIII:C activity.

EXAMPLE 7

Purification of the Factor VIII complex from cryoprecipitate by column chromatography using a linear sodium chloride gradient combined with a convex decreasing pH gradient 60×1.6 cm siliconised column was filled with dextran sulphate Sepharose 4B matrix prepared as in Example 1. The resin was equilibrated at 4° C. with 14 mM trisodium citrate, 2.1 mM calcium chloride in 1.0 M glycine pH 7.3. Two bags of Blood Transfusion Service cryoprecipitate were thawed at 37° C., combined and diluted to 100 ml with equilibrating buffer and adjusted to pH 7.3 with 0.05 M hydrochloric acid. After centrifugation at room temperature to remove any particulate material, 20 ml of the supernatant was diluted to 50 ml and applied to the chromatography column and developed at 4° C. at 42 ml per hour. When all the unbound material was judged to have eluted the bound proteins were developed with a simple two-chamber gradient comprised of 450 ml of the initial equilibrating buffer and 450 ml of 1.0 M glycine, 1.0 M sodium chloride, 2.1 mM calcium chloride pH 5.5, resulting in an elution profile that was linear with respect to sodium chloride concentration, but convex with respect to lowering pH value. As with Example 4 there was good resolution of Factor VIII from most plasma proteins. Fibrinogen eluted at 0.15 M sodium chloride pH 7.0, fibronectin at 0.28 M sodium chloride pH 6.7 and Factor VIII at 0.38 M sodium chloride pH 6.5 with overall yields of 100% Factor VIIIR:Ag, 100% Factor VIIIR:CoF, 65% Factor VIIIC:Ag and 35% Factor VIII:C.

EXAMPLE 8

Purification of Factor VIIIR:Ag and Factor VIIIC:Ag by column chromatography on dextran sulphate coupled to glass beads 2.5 gms. controlled pore glass beads (Electro. Nucleonics Inc., Fairfield, N.J., U.S.A.) mesh size 120/200 with mean pore diameter of 3125 Angstroms were washed and equilibrated with 500 mls. 1% gelatine in 0.05 M phosphate buffer pH 7.2 for two hours at ambient temperature. Glutaraldehyde was added to a final concentration of 1% (vol/vol), left stirring for 5 hours at room temperature, then left for a further 16 hours. The excess protein and glutaraldehyde were removed by washing the beads with 1 M sodium chloride, and finally with distilled water. 20 ml of resuspended beads were added to 100 ml of dextran sulphate (20 mg/ml) and 2 gm cyanogen bromide added with stirring, the pH being maintained at between 10 and 11 through the addition of 4N sodium hydroxide for 30 min. at 4° C. The addition of further sodium hydroxide was stopped and the pH value allowed to stabilise at pH 8.5 for 20 hours at ambient room temperature. The beads were filtered and washed with 1.0 M sodium chloride. The beads were then poured into a 20×0.9 cm siliconised glass column and equilibrated with 14 mM trisodium citrate, 2.14 mM calcium chloride pH 6.85 at ambient room temperature, maintaining a flow rate of 20 ml per hour. 5 ml normal pooled plasma diluted to 15 ml with the equilibrating buffer was applied to the column. After eluting all the void materials, the column was developed using a linear salt gradient of 100 ml. equilibrating buffer plus 100 ml 1.0 M sodium chloride in the same buffer pH 6.85. Good resolution of Factor VIIIR:Ag from fibrinogen was achieved—fibrinogen eluted as a double peak at 0.25 M and 0.3 M sodium chloride, whereas Factor VIIIR:Ag with a yield of 71% eluted as a single component at 0.55 M sodium chloride. The Factor VIIIR:Ag was contaminated with fibronectin which chromatographed as a single component at 0.51 M sodium chloride with a yield of 86%. The Factor VIIIC:Ag was dissociated from the Factor VIIIR:Ag with a total recovery of 55% eluting as a single component at 0.45 M sodium chloride.

EXAMPLE 9

Purification of Factor VIII using "Step-wise" elution from chromatography columns Dextran sulphate Sepharose 4B matrix prepared as in Example 1 was poured into a 3.5 cm long×5.0 cm wide siliconised glass column and eluted at 4° C. at a flow rate of 40 ml per hour using an equilibrating buffer comprised of 1.0 M glycine, 14 mM trisodium citrate and 2.1 mM calcium chloride pH 7.3. Two donations of Blood Transfusion Cryoprecipitate were thawed at 37°

C., the volume adjusted to 100 ml with equilibrating buffer and the pH adjusted to 7.3 using 50 mM hydrochloric acid. After preliminary centrifugation at 2000×g at room temperature to remove any particulate material, 20 ml of the supernatant was diluted to 50 ml with equilibrating buffer and applied to the chromatography column at a constant flow rate of 40 ml per hour, collecting 7.5 ml fractions. After the void material had finished eluting, the column was eluted firstly with an "Intermediate buffer" comprised of 1.0 M glycine, 14 mM trisodium citrate, 2.14 mM calcium chloride and 0.175 M sodium chloride pH 7.0, maintaining the flow rate at 40 ml per hour, and secondly with a "final buffer" comprising 1.0 M glycine, 14 mM trisodium citrate, 2.1 mM calcium chloride, 0.5 M sodium chloride pH 6.2, increasing the flow rate to 200 ml per hour. No detectable Factor VIII, and only 0.04% of the initial fibrinogen was recovered in the void materials eluting from the column. 86% of the initial fibrinogen was eluted by the "intermediate buffer" with only 0.2% of the initial Factor VIIIR:Ag and 7.5% Factor VIIIC:Ag which possessed no detectable Factor VIII:C activity. In contrast the material eluting at the higher flow rate using the "final salt buffer" contained less than 0.2% of the initial fibrinogen, 60% Factor VIIIR:Ag, 20% Factor VIIIC:Ag and 22% Factor VIII:C activity. Analysis of this fraction by high performance liquid chromatography (HPLC) plus ELISA measurements demonstrated that the only major components present other than Factor VIII were the phospholipids. These could be removed by centrifugation of the precipitates formed by treatment with 10% polyethylene glycol 6000 at 65,000×g when the lipoprotein floated to the surface. An alternative "final buffer" solution comprises 1.0 M glycine, 14 mM trisodium citrate, 2.14 mM calcium chloride and 0.5 M sodium chloride pH 7.3, giving similar overall yields.

EXAMPLE 10

Batchwise purification of Factor VIII:vWp

Dextran sulphate Sepharose 4B was made by the Cyanogen bromide method as in Example 1. The matrix was equilibrated at 0.15 M sodium chloride, 14 mM trisodium citrate and 2.14 mM calcium chloride pH 6.85 and mixed with an equal volume of fresh platelet-poor citrated plasma plus two volumes of equilibrating buffer at room temperature. The matrix was gently stirred for 30 minutes and then centrifuged at +10° C. at 3000×g for 10 minutes and the supernatant discarded. The washed dextran sulphate beads were finally suspended in a volume of buffer equal to the original plasma containing 0.80 M sodium chloride and mixed for 30 minutes. The resin was again centrifuged at +10° C. and the supernatant containing the eluted Factor VIII:vWp was removed. The yields of Factor VIIIR:vWp in the batchwise procedure corresponded to 60% of the total applied material.

EXAMPLE 11

Batchwise removal of fibrinogen from cryoprecipitate

Dextran sulphate Sepharose 4B matrix was made by the cyanogen bromide method as in Example 1. 7 ml of the washed resin was resuspended in an equal volume of a buffer comprised of 14 mM trisodium citrate, 2.1 mM calcium chloride pH 6.85 at +4° C. 7 ml of redissolved Blood Transfusion Service cryoprecipitate was added and the tube continuously gently mixed for sixty minutes. The tube was centrifuged at 2000×g at 4° C. for five minutes and the supernatant removed. The gel was resuspended in an equal volume of equilibrating buffer for 5 minutes, centrifuged and the supernatants removed. The fibrinogen content of the combined supernatants accounted for less than 5% of the initial fibrinogen but with 85% of the initial Factor VIIIR:Ag and 50% initial Factor VIII:C. At 4° C. the kinetics of binding of the protein to the matrix is such that fibrinogen binding is rapid whilst that of the Factor VIII complex is slow. Only following incubation with the matrix at 4° C. for 22 hours does greater than 90% of the initial Factor VIII combine with the matrix. The principles of the procedure adopted in this example affords a method of defibrinating whole plasma prior to further purification of the unbound Factor VIII complex.

We claim:

1. A process for the purification of Factor VIII complex, or one or more components thereof, comprising treating an impure preparation of Factor VIII complex with an insoluble matrix having free sulfate groups covalently bound thereto, in a medium of sufficiently high pH and sufficiently low ionic strength for a sufficient period of time to cause a substantial proportion of the Factor VIII complex to bind to said matrix, and subsequently selectively eluting the bound Factor VIII complex or the desired Factor VIII component.

2. A process according to claim 1 wherein the insoluble matrix is dextran sulphate, chondroitin sulphate or sulphated agarose.

3. A process according to claim 1 wherein the desired material is eluted from the insoluble matrix using a buffer of continuously or discontinuously increasing salt concentration.

4. A process according to claim 3, wherein the salt is an ammonium or alkali metal halide, formate, acetate, sulphate or bicarbonate.

5. A process according to claim 1 wherein the desired material is eluted from the insoluble matrix using a buffer of continuously or discontinuously decreasing pH.

6. A process according to claim 1 for purifying Factor VIII-related von Willebrand protein (Factor VIIIR:vWp), wherein Factor VIIIR:vWp is eluted from the insoluble matrix using a buffer having a pH of from 6.0 to 8.0, and a sodium chloride concentration of at least 0.3 M.

7. A process according to claim 6 wherein said buffer has a pH of from 6.7 to 7.0 and a sodium chloride concentration of at least 0.4 M.

8. A process according to claim 1 wherein the initial adsorption of the impure preparation of Factor VIII is conducted at a temperature of from 10° C. to 30° C.

9. A process according to claim 1 wherein the desired material is eluted using a buffer which contains calcium chloride at a concentration of from 1 to 5 mM.

10. A process according to claim 1 wherein the impure preparation of Factor VIII is human plasma or cryoprecipitate obtained therefrom.

11. A process according to claim 1 wherein there is selectively eluted the bound Factor VIII complex.

* * * * *